(12) United States Patent
Zhao (10) Patent No.: US 8,256,896 B2
(45) Date of Patent: Sep. 4, 2012

(54) TORIC OPTIC FOR OPHTHALMIC USE

(75) Inventor: Huawei Zhao, Irvine, CA (US)

(73) Assignee: Abbott Medical Optic Inc., Santa Ana, CA (US)

( * ) Notice: Subject to any disclaimer, the term of this patent is extended or adjusted under 35 U.S.C. 154(b) by 247 days.

(21) Appl. No.: 12/713,046

(22) Filed: Feb. 25, 2010

(65) Prior Publication Data

US 2011/0205486 A1 Aug. 25, 2011

(51) Int. Cl.
*G02C 7/02* (2006.01)

(52) U.S. Cl. ............. 351/159.72; 351/159.38; 623/5.11; 623/6.11

(58) Field of Classification Search .......... 351/159–177, 351/159.01, 159.02, 159.2, 159.38, 159.71, 351/159.72; 623/4.1, 5.11, 6.11, 6.23–6.55
See application file for complete search history.

(56) References Cited

U.S. PATENT DOCUMENTS

| | | | |
|---|---|---|---|
| 4,778,462 A | 10/1988 | Grendahl | |
| 4,795,462 A | 1/1989 | Grendahl | |
| 4,798,608 A | 1/1989 | Grendahl | |
| 4,798,609 A | 1/1989 | Grendahl | |
| 4,898,461 A | 2/1990 | Portney | |
| 4,932,970 A | 6/1990 | Portney | |
| 5,016,977 A | 5/1991 | Baude et al. | |
| 5,066,301 A | 11/1991 | Wiley | |
| 5,479,220 A * | 12/1995 | Komatsu et al. ............. | 351/159 |
| 5,652,638 A | 7/1997 | Roffman et al. | |
| 5,699,142 A | 12/1997 | Lee et al. | |
| 5,796,462 A | 8/1998 | Roffman et al. | |
| 6,142,625 A | 11/2000 | Sawano et al. | |
| 6,457,826 B1 | 10/2002 | Lett | |
| 6,491,721 B2 | 12/2002 | Freeman et al. | |
| 6,533,416 B1 | 3/2003 | Fermigier et al. | |

(Continued)

FOREIGN PATENT DOCUMENTS

EP 949529 A2 10/1999

(Continued)

OTHER PUBLICATIONS

"Accommodation-dependent model of the human eye with aspherics", R. Navarro, J. Santamaria, and J. Bescos, J. Opt. Soc. Am. A, (1985) vol. 2, No. 8, pp. 1273-1281.

(Continued)

*Primary Examiner* — Darryl J Collins
(74) *Attorney, Agent, or Firm* — Abbott Medical Optics Inc.

(57) ABSTRACT

An ophthalmic lens for modifying or reducing non-axisymmetric higher order aberrations includes an optic body disposed about an optical axis having a primary meridian and an orthogonal secondary meridian. The optic body comprises an anterior surface and an opposing posterior surface. The optic body includes an optic zone comprising a base shape that is configured to form an image or focus from light incident on the surfaces, either alone or when used within an optical system. The optic body also includes a higher order toric shape that is imposed on or added to one of the surfaces. The higher order toric shape also includes a first profile disposed along the primary meridian and a second profile disposed along the secondary meridian that is different in shape from the first profile. The higher order toric shape is characterized by a profile along at least one meridian of the lens that changes with increasing radius from the optical axis raised to a power that is greater than two.

20 Claims, 6 Drawing Sheets

U.S. PATENT DOCUMENTS

| | | | |
|---|---|---|---|
| 6,609,793 | B2 | 8/2003 | Norrby et al. |
| 6,808,262 | B2 | 10/2004 | Chapoy et al. |
| 6,923,539 | B2 | 8/2005 | Simpson et al. |
| 6,923,540 | B2 | 8/2005 | Ye et al. |
| 6,986,578 | B2 | 1/2006 | Jones |
| 7,377,640 | B2 | 5/2008 | Piers et al. |
| 2002/0118337 | A1 | 8/2002 | Perrott et al. |
| 2004/0021824 | A1 | 2/2004 | Ye et al. |
| 2004/0080710 | A1 | 4/2004 | Wooley et al. |
| 2004/0150789 | A1 | 8/2004 | Jones |
| 2005/0125056 | A1 | 6/2005 | Deacon et al. |
| 2009/0036980 | A1 | 2/2009 | Norrby et al. |
| 2009/0279048 | A1* | 11/2009 | Hong et al. .................. 351/161 |

FOREIGN PATENT DOCUMENTS

| | | | |
|---|---|---|---|
| WO | WO9303409 | A1 | 2/1993 |
| WO | WO9507487 | A1 | 3/1995 |
| WO | WO0111418 | A1 | 2/2001 |
| WO | WO03009053 | A1 | 1/2003 |
| WO | WO2009020963 | A1 | 2/2009 |
| WO | WO02009137491 | A1 | 11/2009 |

OTHER PUBLICATIONS

"Metrics of optical quality derived from wave aberrations predict visual performance", J.D. Marsack, L.N. Thibos and R. A. Applegate, J. Visual, (2004) 4 (4), pp. 322-328.

"Correlation between Optical and Psychophysical Parameters as a Function of Defocus", E.A. Villegas, C. Gonzalez, B. Bourdoncle, T. Bonnin and P. Artal, Optom. Vis. Sci. (2002) vol. 79, No. 1, pp. 61-67.

"Calculations on the optical modulation transfer function of the human eye for white light", A. van Meeteren, Optica Acta (1974) vol. 21, No. 5, pp. 395-412.

International Search Report and Written Opinion for Application No. PCT/US2011/026193, mailed on Jun. 7, 2011, 17 pages.

International Preliminary Report on Patentability and Written Opinion for Application No. PCT/US09/034555, mailed on Aug. 24, 2010, 8 pages.

International Search Report for Application No. PCT/US09/034555, mailed on May 18, 2009, 5 pages.

International Search Report for Application No. PCT/US2010/038167, mailed on Sep. 27, 2010, 2 pages.

* cited by examiner

TORIC OPTIC FOR OPHTHALMIC USE

BACKGROUND OF THE INVENTION

1. Field of the Invention

The present invention relates generally to ophthalmic lenses, and more specifically to toric ophthalmic lenses such as tonic contact lenses, corneal inlays, and intraocular lenses.

2. Description of the Related Art

Ophthalmic lenses, such as spectacles and contact lenses, may be configured to provide both spherical and cylinder power. The cylinder power of a lens is used to correct the rotational asymmetry aberration of astigmatism of the cornea or eye, since astigmatism cannot be corrected by adjusting the spherical power of the lens alone. Lenses that are configured to correct astigmatism are commonly referred to as tone lenses. As used herein, a toric lens is characterized by a base spherical power (which may be positive, negative, or zero) and a cylinder power that is added to the base spherical power of the lens for correcting the astigmatism of the eye.

Tone lenses typically have at least one surface that can be described by an asymmetric tone shape having two different curvature values in two orthogonal axes, wherein the tonic lens is characterized by a "low power meridian" with a constant power equal to the base spherical power and an orthogonal "high power meridian" with a constant a power equal to the base spherical power plus the cylinder power of the lens. Intraocular lenses, which are used to replace or supplement the natural lens of an eye, may also be configured to have a cylinder power for reducing or correcting astigmatism of the cornea or eye.

In addition to astigmatism, the cornea or eye may also have other higher order aberrations that can degrade optical quality or visual acuity. For example, so called third order, or Seidel, aberrations also include spherical aberration and coma, in addition to astigmatism. As discussed in U.S. Patent Application Number 2009/0279048, which is herein incorporated by reference in its entirety for all purposes as if fully set forth herein, these additional higher order aberrations may be reduced or corrected by introducing an aspheric surface or shape that is characterized by a curvature and conic constant. The aspheric surface may be on the same surface or opposite surface to that of the tonic shape. Thus, the combination of the tone and aspheric shapes provides the possibility of reducing or correcting all third order aberrations of lens itself and/or of cornea or eye.

One problem that has yet to be implemented in to ophthalmic lens design is that the cornea or eye may introduce even higher order aberrations, for example, fifth-order, seventh-order, and ninth-order aberrations. Furthermore, because the cornea may generally have an asymmetric surface shape, the value of these aberrations may vary over different meridians. However, it may be useful to approximate this complexity of the typical cornea by characterizing the higher order aberrations as having different values in orthogonal axes, for example, along the high and low power meridians. While the magnitude of such higher order aberrations may be relatively small compared to third-order or Seidel aberrations, a clinically significant treatment may be provided by correcting these aberrations. Fifth and higher order aberrations cannot generally be reduces by ophthalmic lens surfaces characterized by only a curvature and conic constant. Rather, additional lens or surface design parameters are necessary.

Another problem within the art of ophthalmic lens design is that of identifying average amounts of various aberrations within different populations. Different cornea models have been developed that provide average curvature and conic constant values for populations of human eyes, for example, as disclosed in U.S. Pat. No. 6,609,793, which is herein incorporated by reference in its entirety for all purposes as if fully set forth herein. However, the average spherical aberrations within such populations can vary depending on other variables such as the amount astigmatism, axial length of the eye, average corneal curvature, age, sex, ethnicity, and the like. For example, a subgroup within the population all having about 1 Diopter of astigmatism may have a different amount of spherical aberrations, on average, than another subgroup within the population all having about 3 Diopters of astigmatism. In addition, the average conic may be different between the high and low power meridians, either for the population as a whole or for different subgroups within the population having different amounts of astigmatism or differentiated by some other parameter(s).

Yet another problem may occur in the case of subjects that have previously undergone a corneal refractive procedure, such as LASIK or PRK, and now need or desire to have the natural lens replaced by an intraocular lens. In such cases, the corneal refractive procedure may have been performed on only the central portion of the cornea, for example, out to a diameter of 3 millimeters or 4 millimeters. The border between the treated and untreated portions of the cornea may have relatively discontinuous or large changes in curvature and/or power, which in turn may introduce fifth and higher order aberrations that are different from those in a typical population that has not received a corneal refractive procedure.

For these and other reasons, there is a need for ophthalmic lenses, and methods of design and implementation thereof; that take into account fifth and higher order aberrations of individual, corneas and average corneas representative of a population of eyes. There is also a need for ophthalmic lenses, and methods of design and implementation thereof; that take into account changes in the average aberrations of populations of eyes over changes in certain parameters, such as differing amounts of astigmatism.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION OF THE DRAWINGS

Each and every feature described herein, and each and every combination of two or more of such features, is included within the scope of the present invention provided that the features included in such a combination are not mutually inconsistent.

Embodiments of the present invention are generally directed to toric lenses or surface shapes, and/or related methods and systems for fabrication and use thereof. Toric lenses according to embodiments of the present invention find particularly use in or on the eyes of human or animal subjects. Embodiments of the present invention are illustrated below with particular reference to intraocular lenses; however, other types of lenses fall within the scope of the present invention including, but not limited to, contact lenses, spectacles, phakic intraocular lenses, corneal inlays or onlays, corneal refractive procedures (e.g., LASIK (procedures), and the like.

Embodiments of the present invention include ophthalmic toric lenses and surfaces configured to reduce, or correct, astigmatism and at least one other higher order monochromatic aberration of an individual, average, and/or model cornea or eye. Tone lenses and surfaces according to embodiments of the present invention include a cylinder power and at least one surface comprising an asymmetric aspheric shape characterized by a parameter or coefficient that affects or changes the aspheric shape according to an independent variable (e.g., distance from a center or optical axis) raised to a power that is greater than two, for example, to a power that is greater than or equal to four. Compared to conventional toric lenses, tone lenses according to such embodiments of the present invention advantageously enhance optic quality and/or visual acuity of astigmatic corneas containing fifth and higher order aberrations.

In other embodiments, a tonic lens has an aspheric shape that depends on, or is determined by, the amount of spherical and/or cylinder power of the toric lens. For example, the aspheric shape of the tone lens may be characterized by conic equation, where the value of the conic constant depends on the cylinder power of the lens. In this case, a population of subjects having an astigmatism approximately equal to the cylinder power of the tonic lens have an optical performance or visual acuity that is enhanced in comparison to that provided by a similar tone lens having no aspheric shape, or in comparison to a similar toric lens having an aspheric shape is independent of the cylinder power of the lens. Additionally or alternatively, the tonic lens has an aspheric shape that depends on, or is determined by, some other optical parameter of the toric lens.

As used herein, the term "clear aperture" or "optical zone" means the area of a lens or optic defining the extent of the lens or optic available for forming an image or focus from a collimated or distant light source. The clear aperture or optical zone is usually circular and specified by a diameter. The clear aperture or optical zone may have the same or substantially the same diameter as the optic or lens itself. Alternatively, the diameter of the clear aperture or optical zone may be smaller than the diameter of the optic, for example, due to the presence of a glare or PCO reducing structure that is disposed about a peripheral region of the optic.

As used herein, the term "optical power" means the ability of a lens or optic, or portion thereof, to converge or diverge light to provide a focus (real or virtual), and is commonly specified in units of reciprocal meters ($m^{-1}$) or Diopters (D). When used in reference to an intraocular lens, the term "optical power" means the optical power of the intraocular lens when disposed within a media having a refractive index of 1.336 (generally considered to be the refractive index of the aqueous and vitreous humors of the human eye), unless otherwise specified. See ISO 11979-2, which is herein incorporated by reference in its entirety for all purposes as if fully set forth herein. As used herein the term "focal length" means the reciprocal of the optical power. As used herein the term "power", when used in reference to an optic or lens, means "optical power". As used herein, the term "refractive power" or "refractive optical power" means the power of a lens or optic, or portion thereof, attributable to refraction of incident light. As used herein, the term "diffractive power" or "diffractive optical power" means the power of a lens or optic, or portion thereof, attributable to diffraction of incident light into one or more diffraction orders. Except where noted otherwise, the optical power of a lens or optic is from a reference plane associated with the lens or optic (e.g., a principal plane of an optic).

As used herein, the terms "about" or "approximately", when used in reference to a Diopter value of an optical power, mean within plus or minus 0.25 Diopter of the referenced optical power(s). As used herein, the terms "about" or "approximately", when used in reference to a percentage (%), mean within plus or minus one percent (±1%). As used herein, the terms "about" or "approximately", when used in reference to a linear dimension (e.g., length, width, thickness, distance, etc.) mean within plus or minus one percent (1%) of the value of the referenced linear dimension.

Figure 1:
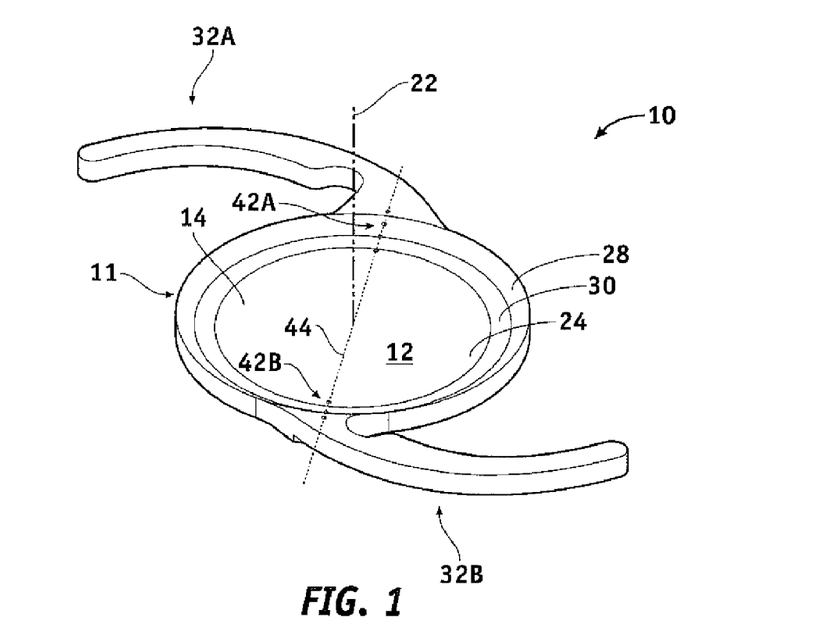
FIG. 1 is a perspective view of the anterior side of an ophthalmic element according to an embodiment of the present invention.
Figure 2:
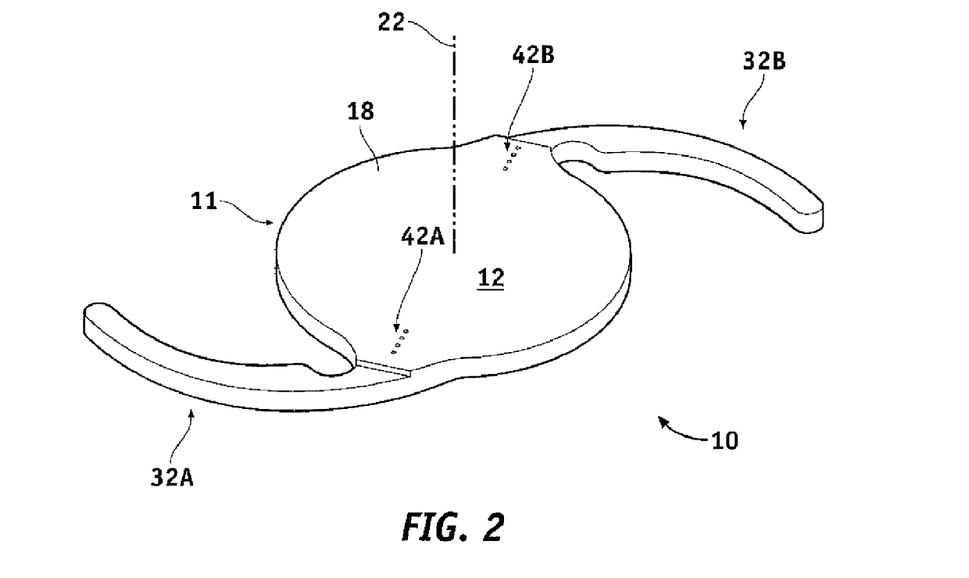
FIG. 2 is a perspective view of the posterior side of the ophthalmic element shown in FIG. 1.

Referring to FIGS. 1 and 2, in certain embodiments, a foldable intraocular lens 10 comprises an optic or optic body 11 including a clear aperture or optical zone 12 and a peripheral zone 13 entirely surrounding optical zone 12. Optic 11 has an anterior surface 14, a substantially opposing posterior surface 18, an optic edge 20, and an optical axis 22. Optic 11 includes a primary meridian and a secondary meridian that is perpendicular to the primary meridian. Anterior surface 14 comprises a central face 24, a peripheral face 28, and a recessed annular face 30 therebetween that is disposed posterior to peripheral face 28. Intraocular lens 10 further comprises haptics 32 (32a, 32b) extending from optic 11 that may optionally be integrally formed with optic 11.

In some embodiments, intraocular lens 10 is a tonic intraocular lens that includes a base toric shape imposed on or added to at least one of surfaces 14, 18. In such embodiments, the base tonic shape includes a low power meridian having a low optical power and a high power meridian having a high optical power equal to the low optical power plus a cylinder optical power. The high power meridian may be disposed along the primary or secondary meridian, or may be a some angle between the primary and secondary meridians, for example, and a 45 degree angle from the primary or secondary meridian. In the illustrated embodiment, intraocular lens 10 also comprises a first mark 42a and a second mark 42b, which may be configured for use in angularly aligning toric intraocular lens 10 in the eye and are disposed along, or form, an imaginary line 44 when viewed from anterior side 14 or posterior side 18 of intraocular lens 10.

A detailed description of various elements and features of intraocular lens 10, as shown in FIGS. 1 and 2, may be found in U.S. Patent Application Publication 2005/0125056 and U.S. patent application Ser. No. 12/620,765, both of which are herein incorporated by reference in their entirety for all purposes as if fully set forth herein. Various structural features of intraocular lens 10 shown in FIGS. 1 and 2 are exemplary, and other optic body and haptic structures are within the scope of embodiments of the present invention.

In the illustrated embodiment, optic 11 is commonly circular and may be constructed of at least one of the materials commonly used for resiliently deformable or foldable optics, such as silicone polymeric materials, acrylic polymeric materials, hydrogel polymeric materials, such as polyhydroxyethylmethacrylate, polyphosphazenes, polyurethanes, and mixtures thereof and the like. Alternatively, optic 11 may be constructed of at least one of the commonly employed material or materials used for rigid optics, such as polymethylmethacrylate (PMMA). In some embodiments, optic 11 is made of SENSAR® brand of acrylic. Other advanced formulations of silicone, acrylic, or mixtures thereof are also anticipated. Optic 11 material may be selected such that optical zone 12 is optically clear and exhibits biocompatibility in the environment of the eye. Foldable/deformable materials are particularly advantageous since optics made from such deformable materials may be rolled, folded or otherwise deformed and inserted into the eye through a small incision. The lens material may have a refractive index provides a relatively thin, flexible optic section, for example, having a center thickness that is from 150 micrometers to 1000 micrometers, depending on the material and the base optical power of optic 11. For example, in one embodiment, optic 11 is made of Sensar® brand of acrylic and a base optical power of 20D. In such embodiment, optic 11 has a center thickness $T_c$ that may be from 0.4 millimeter to 1.5 millimeter. The center thickness $T_c$ may vary from this range, depending on factors such as the lens material and the dioptric power of optical zone 12, or the use of diffractive surfaces or profiles. Optic 11 may have a diameter that is from 4 millimeters to 8 millimeters, or more. As used herein the term "thickness", when used in reference to lens or optic, generally refers to a dimension in a direction that is along, or substantially along, an optical axis about which the lens or optic is disposed.

Intraocular lens 10 may comprise any of the various means available in the art for centering or otherwise locating or supporting optical zone 12 within the eye. In the illustrated embodiment haptics 32 are used for centering intraocular lens 10 within the eye; however, other types of support structure may be used, for example, as typically used for supporting an optic or optics of an accommodating intraocular lens. Haptics 32 of the illustrated embodiment may be integrally formed of the same material as optic 11 to faun a one-piece IOL. Alternatively, haptics 32 may be integrally formed in a common mold with optic 11, but be made of a different material than optic 11. In other instances, haptics 32 is &mined of the same material as optic 11, but haptics 32 and optic 11 materials have different states, for instance differing amounts of water content or percentage of a cross-linked polymer. Additionally or alternatively, haptics 32 may be formed separately from optic 11 and subsequently attached to optic 11 to provide a three-piece configuration. Haptics 32 may comprise any of a variety of materials which exhibit sufficient supporting strength and resilience, and which are substantially biologically inert in the intended in vivo or in-the-eye environment. Suitable materials for this purpose include, for example, polymeric materials such as polypropylene, PMMA, polycarbonates, polyamides, polyimides, polyacrylates, 2-hydroxymethylmethacrylate, poly (vinylidene fluoride), polytetrafluoroethylene and the like; and metals such as stainless steel, platinum, titanium, tantalum, shape-memory alloys, e.g., nitinol, and the like. In other embodiments, intraocular lens 10 comprises a positioning means that allows optic 11 to move along optical axis 22 or be deformed in response to deformation of the capsular bag and/or in response to the ciliary muscles of the eye.

Optical zone 12 may include various forms suitable for providing vision to a subject. For example, optical zone 12 may be biconvex, plano-convex, plano-concave, meniscus, or the like. The base optical power of optical zone 12 may be either positive or negative. The general shape of posterior surface 18 and central face 24 of anterior surface 14 may include any shape generally used for producing an optic portion configured to focus, or form an image from, light incident on the optic. For instance, one of surfaces 14, 18 may be spherical with an overall radius of curvature that is either positive or negative. The shape of at least one of surfaces 14, 18 is aspheric, as discussed in greater detail below herein. One or both surfaces 14, 18 may be optionally configured to provide more than one focus, for example to correct for both near and distant vision as described by Portney in U.S. Pat. No. 4,898,461. Optical zone 12 may be configured as part of a lens system (e.g., a two optic system) and/or for providing accommodative vision (e.g., by being made of a material that can change shape to provide varying base optical power in response to an ocular force).

At least portions of posterior surface 18 and/or central face 24 of optical zone 12 may comprise one or more optical phase plates. In such embodiments, the total base optical power of optical zone 12 is a combination of the base refractive power of posterior surface 18 and central face 24, and the diffractive optical power of the one or more diffraction orders produced by the one or more phase plates. The one or more phase plates may be either a monofocal phase plate providing one dominant diffraction order or a multifocal phase plate, such as a bifocal phase plate, for providing, for instance, simultaneous near and distant vision. Other types of phase plates may also be used. For example, the phase plate may be based on a change in the refractive index of the material used to form optical zone 12.

The total base optical power of optical zone 12 may be from +2 Diopters to +50 Diopters, or more, commonly within a range of +5 Diopters to +40 Diopters, or a range of +5 Diopters to +30 Diopters. The total base optical power of optical zone 12 may be either positive or negative, for instance within a range of −15 Diopters or to +50 Diopters or more, or within a range of −10 Diopters to +40 Diopters. Other ranges of refractive optical power may be preferred, depending on the particular application and type of intraocular lens to be used. As discussed above herein, when referring to an intraocular lens, the base powers discussed in this paragraph generally refer to the optical power of the intraocular lens when disposed within a surrounding media having a refractive index of 1.336.

At least one of surfaces 14, 18 includes a higher order toric shape imposed on, added to, or combined with one of surfaces 14, 18. The higher order toric shape is non-axisymmetric so that optic 11 may be configured reduce or correct ocular aberrations that are not treated using prior art lenses. As used herein, the term "non-axisymmetric", when applied to a surface shape or profile, means a surface in which the shape or profile various meridians through the optical axis of the surface is different and/or depends on the angle of the meridian relative to a reference meridian or axis. The base tone shape and the higher order toric shape may be disposed on opposite surfaces of surfaces 14, 18. Alternatively, the base toric shape and the higher order tonic shape may both be disposed on a same surface 14 or 18. The higher order toric shape is characterized by a profile along at least one meridian that changes with increasing radius from the optical axis raised to a power that is greater than two, for example, is characterized by a profile along at least one meridian that changes with increasing radius from the optical axis raised to a fourth, sixth, and/or higher power. As used herein the "order" or "power" of a polynomial term within a polynomial equation is the sum of the powers of each independent variable within the polynomial term. In the case of polynomial having two independent variables (e.g., x and y along axes perpendicular to an optical axis), the "order" or "power" of a polynomial term is the sum of the powers of the x and y variable within the polynomial term. For example, profiles that change with increasing radius from the optical axis raised to a fourth power include surfaces described by terms including $x^4$, $y^4$, $x^2y^2$, $xy^3$, $x^3y$, where x and y are coordinate along two axes of optic zone 12 that are perpendicular to an optical axis of optic zone 12 (e.g., a z-axis). Examples of profiles that change with increasing radius from the optical axis raised to a sixth power include surfaces described by terms including $x^6$, $y^6$, $x^2y^4$, $x^4y^2$, $x^3y^3$, and the like.

Advantageously, the non-axisymmetric characteristics of the higher order toric shape may be configured to reduce fifth-order and/or higher optical aberrations of a cornea or eye into which toric intraocular lens 10 is placed. Additionally or alternatively, the non-axisymmetric characteristics of the higher order toric shape may be configured so that optic zone 12 reduces a fifth-order or higher optical aberration of an average cornea or eye of a particular population of eyes. In certain embodiments, intraocular lens 10 does not include the base toric shape, for example, in cases where the cornea being corrected has higher order aberrations that are non-axisymmetric, but no astigmatism or an astigmatism that is less than or equal to 0.25 Diopters or is less than or equal to 0.5 Diopters.

The overall shape of an optic surface containing the base toric shape and/or the higher order toric shape may be regarded as the superposition of either or both toric shapes with a surface shape of that optic surface. The base surface shape may be planer or spherical and characterized by a constant curvature or radius of curvature. Alternatively, the base surface may have an axisymmetric aspheric shape, for example, configured to reduce a symmetrical third order aberration of optic zone 12 and/or of an eye into which intraocular lens 10 is to be placed. Additionally or alternatively, the aspheric base surface may be configured to provide some other optical effect, for example, to provide an increased or enhanced depth of focus or to provide a multifocal lens (either refractive or diffractive).

In some embodiments, the base toric shape and/or the higher order toric shape is located on one of surfaces 14, 18, while the opposite surface 18, 14 includes axisymmetric aspheric shape (e.g., to reduce a spherical aberration of the lens 10 or eye, provide an increased depth of focus, and/or provide a multifocal lens). Alternatively, the base toric shape and/or the higher order toric shape may be combined with or added to the axisymmetric aspheric shape on a single surface of optic zone 12.

In certain embodiments, the axisymmetric aspheric shape may be characterized by a conoid of rotation, wherein a surface sag profile along any meridian varies according to the equation:

$$z = \frac{cr^2}{1 + \sqrt{1 - (1+k)c^2r^2}} \quad (1)$$

where z is the surface sag along a z-axis, r is the radial distance from the optical axis 22, c is a base curvature of the surface (which is equal to 1/R, where R is the radius of curvature), and k is a conic constant of the surface. Alternatively, at least one of the surfaces of intraocular lens 10 may be characterized by a modified conoid of rotation, wherein the surface sag profile along any meridian varies according to the relation:

$$z = \frac{cr^2}{1 + \sqrt{1 - (1+k)c^2r^2}} + a_4r^4 + a_6r^6 + \ldots \quad (2)$$

where $a_2, a_4, \ldots$ are constants, c is a base curvature of the surface (which is equal to 1/R, where R is the radius of curvature, k is a conic constant, and r is the radial distance from the optical axis 22. For Equations 1 and 2, as well as for other embodiments discussed below, the z-axis may be parallel to optical axis 22. Alternatively, the z-axis may have an offset angle from the optical axis 22.

In some embodiments, a surface sag profile of at least one of surfaces 14, 18 is characterized by the equation:

$$z = \frac{cr^2}{1 + \sqrt{1 - (1+k)c^2r^2}} + A_{20}x^2 + A_{11}xy + A_{02}y^2 + A_{40}x^4 + \\ A_{04}y^4 + A_{22}x^2y^2 + A_{60}x^6 + A_{06}y^6 + A_{42}x^4y^2 + A_{24}x^2y^4 \quad (3)$$

where x and y are coordinate values along an x-axis and a y-axis, respectively, z is a surface sag coordinate value along a z-axis perpendicular to the x and y axes, $r^2$ is equal to $x^2+y^2$, c is a base curvature, k is a conic constant, and $A_{20}$, $A_{11}$, $A_{02}$, $A_{40}$, $A_{04}$, $A_{22}$, $A_{60}$, $A_{06}$, $A_{42}$, and $A_{24}$ are polynomial coefficients of the equation. The coefficients $A_{20}$, $A_{11}$, $A_{02}$ may be used to characterize the base toric shape, while the coefficients $A_{40}$, $A_{04}$, $A_{22}$, $A_{60}$, $A_{06}$, $A_{42}$, and $A_{24}$ may be used to characterize the higher order toric shape. Since the polynomial in Equation (3) includes polynomial terms containing both x and y variables, the polynomial coefficients may be selected so that the higher order toric shape is non-axisymmetric. Thus, the higher order toric shape may be configured so that the profile along various meridians change or vary with angle relative to a reference axis (e.g., the x-axis or y-axis). For example, a non-axisymmetric higher order toric shape may be defined when $A_{40}$ is unequal to $A_{04}$, when $A_{60}$ is unequal to $A_{06}$, or when $A_{22}$, $A_{42}$, and/or $A_{24}$ have non-zero values. Advantageously, the non-axisymmetric form of the higher order toric shape make more design variables available for reducing fifth and higher order corneal aberrations than does an axisymmetric shape, the latter being characterized by polynomial terms having only one independent variable (e.g., radius r from optical axis 22). The additional fourth and sixth order design variables aid, for example, in reducing fifth and higher order aberrations—especially asymmetric fifth and higher order aberrations. Such aberrations cannot be adequately reduced using optical elements that only include a spherical power and toric power oriented along a particular meridian, even when incorporating one or more conic constants for reducing third order aberrations such as lower order spherical aberrations. The polynomial portion of Equation (3) may also contain additional higher order terms (e.g., terms including $x^8$, $y^8$, $x^6y^2$, $x^2y^6$, $x^4y^4$, $x^{10}$, and the like) as desired for reducing or balancing even higher order corneal aberrations. In certain embodiments, a polynomial surface profile or shape has one or more eighth and/or sixteenth order polynomial terms—either alone or in combination with other higher order terms—that are configured or selected to reduce or modify fourth or fifth order aberrations, respectively, of an incident wavefront.

Alternatively, if intraocular lens 10 is used a cornea having higher order aberrations, but no or little astigmatism, the surface sag profile of at least one of surfaces 14, 18 is characterized by the equation:

$$z = \frac{cr^2}{1+\sqrt{1-(1+k)c^2r^2}} + A_{40}x^4 + A_{04}y^4 + \\ A_{22}x^2y^2 + A_{60}x^6 + A_{06}y^6 + A_{42}x^4y^2 + A_{24}x^2y^4 \quad (4)$$

where x and y are coordinate values along an x-axis and a y-axis, respectively, z is a surface sag coordinate value along a z-axis perpendicular to the x and y axes, $r^2$ is equal to $x^2 + y^2$, c is a base curvature, k is a conic constant, and $A_{40}$, $A_{04}$, $A_{22}$, $A_{60}$, $A_{06}$, $A_{42}$, and $A_{24}$ are polynomial coefficients of the equation, which may be selected to characterize the higher order toric shape of lens surface 14 and/or 18.

All of the options and combinations discussed above are available to a designer through use of the surface definition provided by Equations (3) and (4). This gives designers great flexibility in reducing, compensating for, and/or balancing both third order and higher order corneal aberrations, particularly in the case of asymmetric or non-axisymmetric higher order aberrations.

In another alternative to Equation (3), a surface sag profile of at least one of surfaces 14, 18 may be characterized by the equation:

$$z = \frac{c_1x^2 + c_2y^2}{1+\sqrt{1-(1+k_1)c_1^2x^2+(1+k_2)c_2^2x^2}} + A_{40}x^4 + \\ A_{04}y^4 + A_{22}x^2y^2 + A_{60}x^6 + A_{06}y^6 + A_{42}x^4y^2 + A_{24}x^2y^4 \quad (5)$$

where x and y are coordinate values along an x-axis and a y-axis, respectively, z is a surface sag coordinate value along a z-axis perpendicular to the x and y axes, $r^2$ is equal to $x^2 + y^2$, where $c_1$ is the base curvature along a first meridian of optic body 11, $k_1$ is the conic constant along the first meridian, $c_2$ is the base curvature along a second meridian of optic body 11, $k_2$ is the conic constant along the second meridian, and $A_{40}$, $A_{04}$, $A_{22}$, $A_{ho}$, $A_{06}$, $A_{42}$, and $A_{24}$ are polynomial coefficients of the equation. The coefficients $c_1$ and $c_2$ may be used to characterize the base toric shape, while the coefficients $A_{40}$, $A_{04}$, $A_{22}$, $A_{60}$, $A_{06}$, $A_{42}$, and $A_{24}$ may be used to characterize the higher order toric shape. The two conic constant coefficients $k_1$ and $k_2$ may be used to independently introduce differing amounts of third order aberration along two orthogonal axis of intraocular lens 10. Similar to Equation (2), the polynomial in Equation (3) includes polynomial terms containing both x and y variables, so that the coefficients may be selected to make the higher order toric shape non-axisymmetric. For example, a non-axisymmetric higher order toric shape may be defined when $A_{40}$ is unequal to $A_{04}$, when $A_{60}$ is unequal to $A_{06}$, or when $A_{22}$, $A_{42}$, and/or $A_{24}$ have non-zero values.

In certain embodiments, the surface sag profile of at least one of surfaces 14, 18 includes polynomial terms in which x and/or y are raised to an odd valued power (e.g., 1, 3, and/or 5). Such odd valued power terms provide a surface having a shape that is not only asymmetric in the sense that the profile or shape along different meridians changes with angular orientation about the optical axis, but is also asymmetric along one or more individual meridians. That is, for a surface characterized by a polynomial term having an odd valued power variable (e.g., x, or y in the above equations), at least one meridian of the surface will have a shape or profile that is different on each side of the optical axis.

Figure 3A:
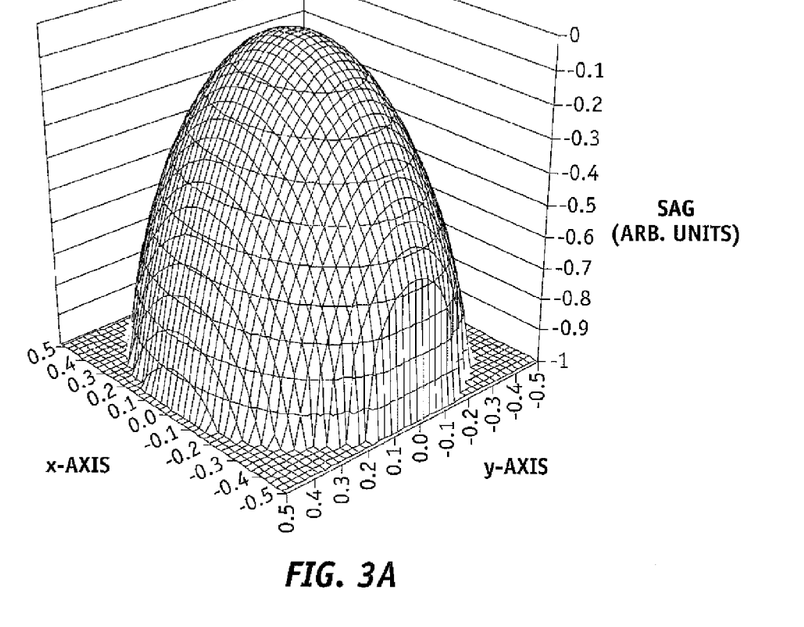
FIGS. 3A and 3B are three dimensional and two dimensional plots of an optic surface.
Figure 3B:
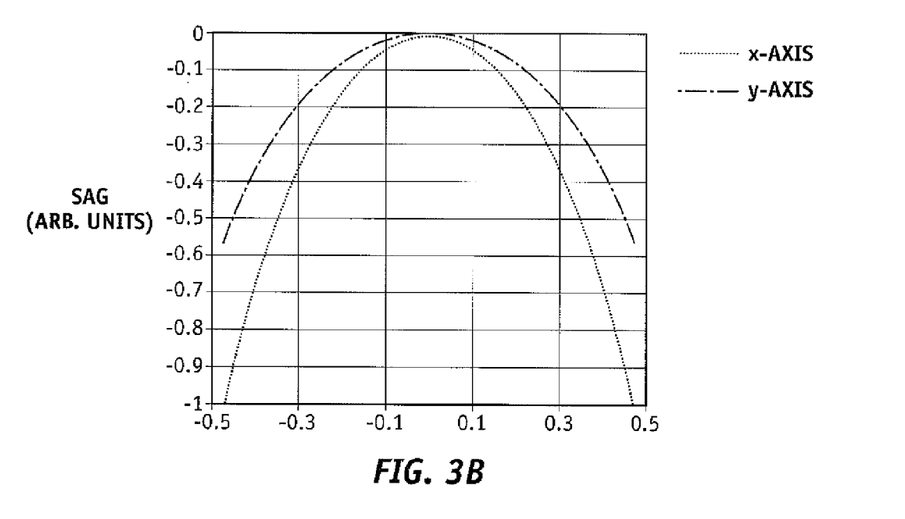
Figure 4A:
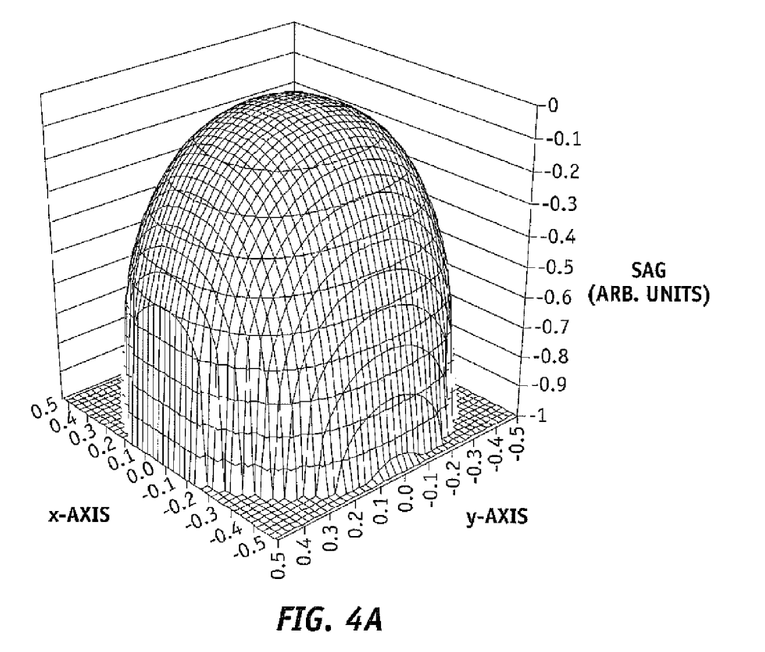
FIG. 4A and 4B are similar to FIGS. 3A and 3B, but also include higher order polynomial terms.
Figure 4B:
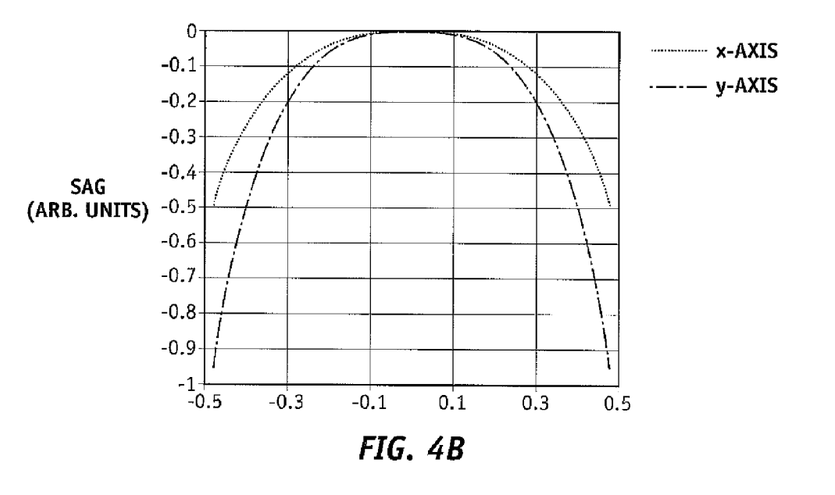
Figure 5A:
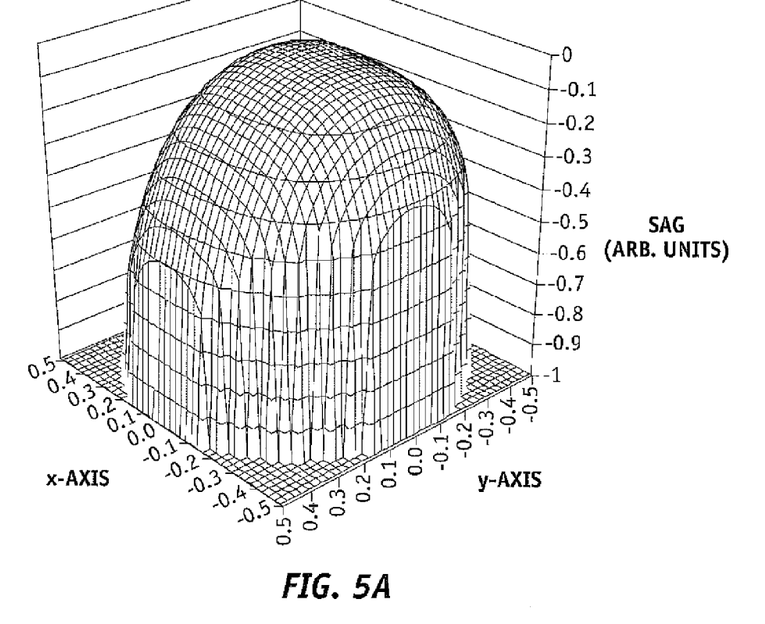
FIG. 5A and 5B are similar to FIGS. 4A and 3B, but introduce a third order polynomial term.
Figure 5B:
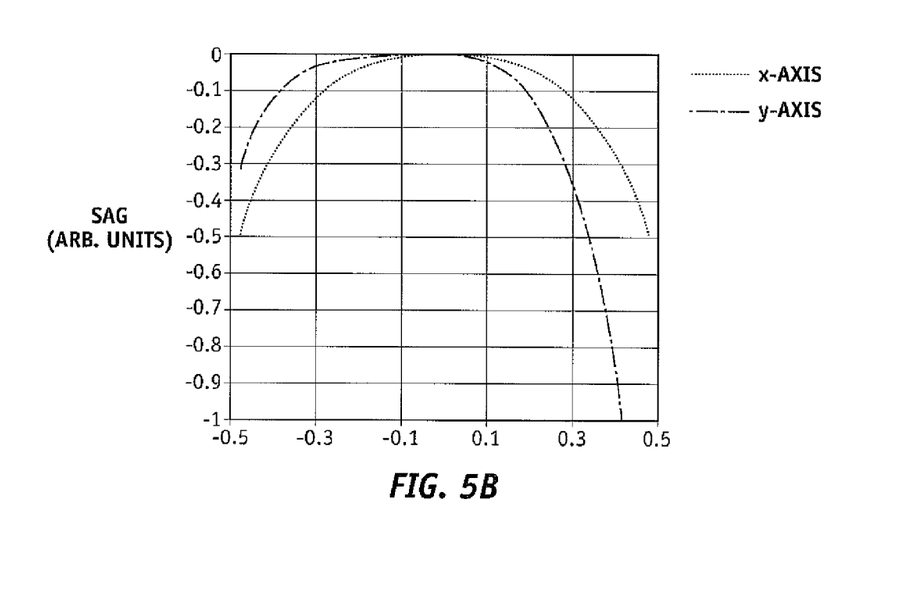

Referring to FIGS. 3-5, various shape and profile features of surfaces according to embodiments of the invention will now be discussed. The plots shown in FIGS. 3-5 are based on the equation::

$$z = \frac{cr^2}{1+\sqrt{1-(1+k)c^2r^2}} + A_{20}x^2 + A_{02}y^2 + A_{03}y^3 + A_{40}x^4 + A_{04}y^4. \quad (6)$$

The base surface in these examples is spherical (i.e., the conic constant, k, is equal to zero). The plots are based on an aperture having a diameter of 1 arbitrary unit. The vertical axis is also in arbitrary units and the scale is exaggerated to demonstrate the features of each design. The coefficient values for each plot are shown in Table 1. In discussing these figures, the x-axis will be referred to as the primary meridian and the y-axis will be referred to as the secondary meridian.

TABLE 1

Coefficient values for the plots shown in FIGS. 3-5.

| | FIG. 3 | FIG. 4 | FIG. 5 |
|---|---|---|---|
| c (curvature) | 2 | 2 | 2 |
| k (conic const.) | — | — | — |
| A.20 | 3 | — | — |
| A.02 | 1 | — | — |
| A.03 | — | — | 6 |
| A.40 | — | 3 | 3 |
| A.04 | — | 12 | 12 |

Referring to FIGS. 3A and 3B, a standard toric surface is shown in which the primary meridian (x-axis) has a higher optical power than the secondary meridian. FIG. 3A shows a three dimensional plot of the surface shape, while FIG. 3B shows a two-dimensional plot of the surface profiles along the primary and secondary axes. As seen in FIG. 3B, each profile has a parabolic shape imposed on or added to a base spherical surface having a curvature of 2.

FIGS. 4A and 4B show the same type plots as those in FIGS. 3A and 3B, but the standard toric shape (defined by A.20 and A.02) is replace with two fourth order terms. As seen in FIG. 4B, the slope near the center along the two profiles is less near the center than in the case of FIG. 3B. However, the slope increases more rapidly at the periphery in FIG. 4B than in FIG. 3B. The surface in FIGS. 4A and 4B also has the same base spherical shape, and thus illustrate a spherical surface that is influenced more by the fourth order terms as the radius from the center of the surface increases. Such a surface may be suited for correction aberrations of a generally spherical cornea, but which has higher order spherical aberrations. A base toric surface like than shown in FIGS. 3A and 3B may also be added to the surface in FIGS. 4A and 4B, which would additional correct for a lower order astigmatism of the cornea.

FIGS. 5A and 5B are similar to those shown in FIGS. 4A and 4B; however, an asymmetric third order term has been introduced along the secondary meridian. While the primary meridian is still symmetric about the center, the secondary meridian is clearly asymmetric about the center of the surface. Such a surface may be well suited to correct both coma and higher order astigmatisms.

Figure 6:
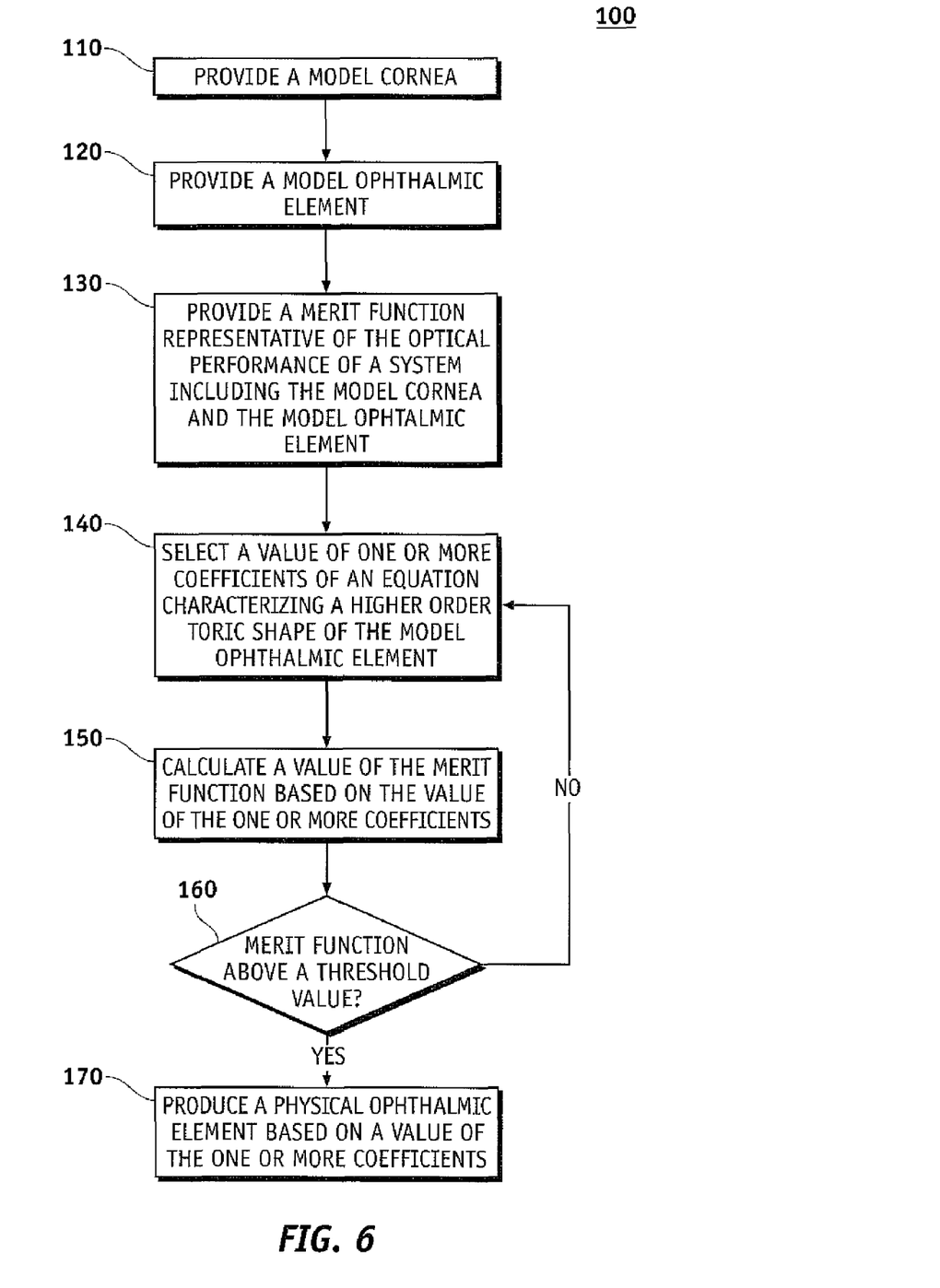
FIG. 6 is a flow chart illustrating a method of providing an ophthalmic element according an embodiment of the present invention.

Referring to FIG. 6, a method 100 may be used to provide an ophthalmic element according an embodiment of the present invention. The method 100 may be used, for example, to provide various embodiments of the intraocular lens 10 discussed above. Alternatively, method 100 may be used to provide other ophthalmic lenses such as corneal implants, contact lenses, spectacles, or the like.

Using the intraocular lens 10 as an example, method 100 comprises an element 110 that includes providing a model cornea. Method 100 also comprises an element 120 that includes providing a model ophthalmic element according to an embodiment of the present invention. Method 100 additionally comprises an element 130 that includes providing a merit function representative of the optical performance of a system including the model cornea and the model ophthalmic element. Method 100 also comprises an element 140 that includes selecting a value of one or more coefficients of an equation characterizing the higher order toric shape of the model ophthalmic element. Method 100 further comprises an element 150 that includes calculating a value of the merit function based on the value of the one or more coefficients, and an element 160 that includes determining whether the value of the merit function is above a predetermined value. Method 100 further comprises an element 170 that includes producing a physical ophthalmic element based on a value of the one or more coefficients that causes the merit function to be above the threshold value.

Element 110 of method 100 includes providing the model cornea. The model cornea may be a physical model of the cornea of a human or animal eye, wherein the model cornea is part of a system that also contains at least one light sources and an electronic or photographic detector that may be used to evaluate images formed by the model cornea. Alternatively, the model cornea may comprise various parameters of an optical program or electronic model utilized to calculate or evaluate the optical performance of the cornea in conjunction with an ophthalmic element according to an embodiment of the present invention. In either case, the model cornea may be characterized by various parameters or features that produce aberrations to be corrected or reduced by an ophthalmic element such as the intraocular lens 10. For example, the model cornea may be characterized an aspheric profile along a first meridian of the model cornea that is different from an aspheric profile along a second meridian of the model cornea. Additionally or alternatively, the model cornea may be characterized by higher order aberration, for example, a fifth-order aberration, seventh-order aberration, and/or ninth-order aberration. Additionally or alternatively, the model cornea may be characterized by an asphericity of a first zone of the model cornea that is different from an asphericity of a second zone of the model cornea surrounding the first zone. Such a model cornea may be used simulate or evaluate corneas which have undergone a refractive surgical procedure.

In certain embodiments, element 110 additionally or alternatively includes providing an eye model, of which the model cornea may be a part. For example, the model cornea may incorporate average characteristics or values of parameters characterizing the corneas of people or animals over a certain age, people or animals that are candidates for a surgical procedure (e.g., a cataract and/or corneal refractive procedure), people or animals that are that have an astigmatism, or correction cylinder power, falling within a certain range and/or offset angle (e.g., an astigmatism, or correction cylinder power, between 0.5 and 1.5 Diopters, between 1.5 and 2.5 Diopters, between 1.5 and 3 Diopters, or greater than 3 Diopter or 4 Diopters), and the like. The eye model may take into account physical and optical characteristics for a given population. For example, the eye model may be based on the Navarro eye model, as disclosed in "Accommodation-dependent model of the human eye with aspherics", J. Opt. Soc. Am. A, Vol. 2, No. 8, pp. 1273-1281, which is herein incorporated by reference in its entirety for all purposes as if fully set forth herein. Alternatively, the eye model may be one of those disclosed in U.S. Pat. Nos. 6,609,793 or 7,377,640, which are herein incorporated by reference in their entirety for all purposes as if fully set forth herein. In some embodiments, the model cornea is characterized by Equations (1) or (2) above, where the pupil has a 5 millimeter diameter, the model cornea has a radius of curvature of 7.553 millimeters and a conic constant of −0.1034, and the eye has a refractive index 1.3375, as disclosed in U.S. Pat. No. 6,609,793. Rather than being based on average values from a population, element 110 may provide a model cornea or eye model that is based on optical and/or physical measurements of an individual human or animal eye, wherein a custom ophthalmic element may be provided.

Element 120 of method 100 includes providing a model ophthalmic element, for example, an embodiment of the intraocular lens 10 discussed above. The model ophthalmic element may be characterized by a higher order toric shape that is imposed on, or added to, a surface of the model ophthalmic element. The higher order toric shape includes a primary meridian characterized by a first profile and a secondary meridian characterized by a second profile that is different from the first profile. The higher order tonic shape may be characterized by a profile along at least one meridian that changes according to radius from the optical axis raised to a power that is greater than two.

Element 130 of method 100 includes providing a merit function representative of the optical performance of a system including the model cornea and the model ophthalmic element. The merit function may incorporate, or be based on, the performance of a lens, optic, surface, or system that is defined, expressed, or quantified as an MTF that is above a predetermined threshold value (e.g., 0.05, 0.10, 0.15, 0.17, 0.20, 0.25, or higher) at a particular frequency (e.g., 25, 50, or 100 line pairs per millimeter). As expressed herein, the performance of a lens, optic, or surface according to embodiments of the present invention may be expressed or quantified in terms of through-focus MTF data at a particular spatial frequency. For example, the depth of focus may be defined as the region in a through-focus plot over which the Modulation Transfer Function (MTF) at a spatial frequency of 50 line pairs per millimeter exceeds a selected cutoff value. Typical cutoff values may include 0.05, 0.10, 0.15, 0.17, 0.20, 0.25, or higher. Other spatial frequencies may include 25 line pairs per millimeter or 100 line pairs per millimeter. Another way to define the depth of focus is based on a relative threshold, where the threshold is defined based on a peak value of a figure of merit. For instance, the depth of focus may be defined as the full width at half max (FWHM) of the MTF at a particular spatial frequency. Other relative thresholds may be 95%, 90%, 80%, 70%, 60%, 50%, 1/e, $1/e^2$ of a peak value of the MTF, or any suitable fraction of the peak value of MTF or another metric.

The performance of a lens, optic, surface, or system may be defined, expressed, or quantified as an MTF performance over a range of focal length, for example, to provide a lens having an extended or enhanced depth of focus compared to another lens that is similar, but does not incorporate features or elements of a lens configured according to an embodiment of the present invention. The performance may be over a defocus range expressed in terms of object space distances, image space distances, or Diopter power. In some embodiments, a lens, optic, or surface may be specified in terms of an increase in depth of focus as compared to the corresponding reference optic, either in absolute terms (e.g., an increased defocus range compared to the reference optic over which a predetermined MTF performance is maintained) or in relative terms (e.g., a percent increase in defocus range as compared to a reference optic, such as a 10%, 20%, 50%, 100%, 200%, or greater increase in defocus range as compared to a reference optic).

Additionally, performance of a lens, optic, surface, or system may be defined, expressed, or quantified in terms of an axial distance, or, equivalently, in terms of a power. The figures of merit, or metrics, may be either purely optical in nature, or may incorporate some perception effects from the human eye. For instance, any or all of the following optical metrics may be used: MTF at a particular spatial frequency, MTF volume (integrated over a particular range of spatial frequencies, either in one dimension or in two dimensions), Strehl ratio, encircled energy, RMS spot size, peak-to-valley spot size, RMS wavefront error, peak-to-valley wavefront error, and edge transition width. Additionally or alternatively, any of the following psychophysical metrics may be used: contrast sensitivity, visual acuity, and perceived blur. Additionally or alternatively, other metrics found in the literature may be used, such as those detailed in Marsack, J. D., Thibos, L. N. and Applegate, R. A., 2004, "Metrics of optical quality derived from wave aberrations predict visual performance," J Vis, 4 (4), 322-8; Villegas, E. A., Gonzalez, C., Bourdoncle, B., Bonnin, T. and Artal, P., 2002, "Correlation between optical and psychophysical parameters as a function of defocus," Optom Vis Sci, 79 (1), 60-7; van Meeteren, A., "Calculations on the optical transfer function of the human eye for white light," Optica Acta, 21 (5), 395-412 (1974), all of these references being herein incorporated by reference in its entirety for all purposes as if fully set forth herein.

Any or all of the above performance definitions or criteria may be characterized at a single wavelength, such as 550 nm or any other suitable wavelength, at a plurality of selected wavelengths, or over a spectral region, such as the visible spectrum from 400 nm to 700 nm. The performance metrics may be weighted over a particular spectral region, such as the weighting associated with the spectral response of the human eye. It will be appreciated that the above criteria may be used in determining or comparing the performance of any of the optic discussed herein.

Element 140 of method 100 includes selecting a value of one or more coefficients or parameters of an equation characterizing the higher order toric shape imposed on a surface of the model ophthalmic element. Alternatively, the value of parameters may be selected that are representative of other shapes imposed on the same, or a different, surface of the model ophthalmic element, either independently or in conjunction with the coefficients for the higher order toric shape. For example, parameters of one or more of Equations (1) through (5) may be selected.

Once a merit function has been determined and coefficient values of an equation characterizing the ophthalmic element have been selected, element 150 of method 100 includes calculating a value of the merit function based on initial value(s) of the coefficient(s) or parameter(s). Element 160 includes determining whether the value of the merit function is above a predetermined or threshold value. If the merit function is not above the predetermined or threshold value, then elements 140 and 150 are repeated wherein one or more coefficient or parameter values are changed. Once as set of coefficients or parameter provide a merit function value that is above the selected threshold or predetermined value, the element 170 of method 100 includes producing a physical ophthalmic element based on the value of the first coefficient. The physical ophthalmic element may be an intraocular lens such as an embodiment of intraocular lens 10 discussed above. Alternatively, the physical ophthalmic element may be a spectacle lens, a contact lens, a corneal implant, or the like. Additionally or alternatively, the physical ophthalmic element may include a modification of the natural, for example, a corneal refractive procedure such as a LASIK or PRK procedure on the cornea on an eye.

As used herein, a merit function for an optical element or system is "above a threshold value" or "above a predetermined value" when the optical element or system has a more favorable or desirable optical performance than it would have if the optical element or system were modified to have a merit function equal to the threshold or predetermined value. For example, the "threshold value" of an optical system may be selected to be an MTF 0.2 at a frequency of 50 line pairs per millimeter. In this case, the system merit function would be "above the threshold value" if the actual or calculated system MTF were greater than 0.2 (e.g., if the system had an MTF of 0.21, 0.25, or 0.3 at 50 line pairs per millimeter), since a higher MTF is commonly considered to represent better optical system performance. In another example, the "threshold values" of an optical system may be selected to be an image spot diameter of 20 micrometers. In this case, the system merit function would be "above the threshold values" if the actual or calculated system image spot diameter were less than 20 micrometer (e.g., if the system produced a spot diameter of 18 micrometers or 10 micrometers), since a smaller spot diameter is commonly considered to represent better optical system performance. These two examples demonstrate that a particular merit function may represent better optical performance as the value of the merit function increases in value, or as the value of the merit function decreases in value, depending on the units of the merit function.

Figure 7:
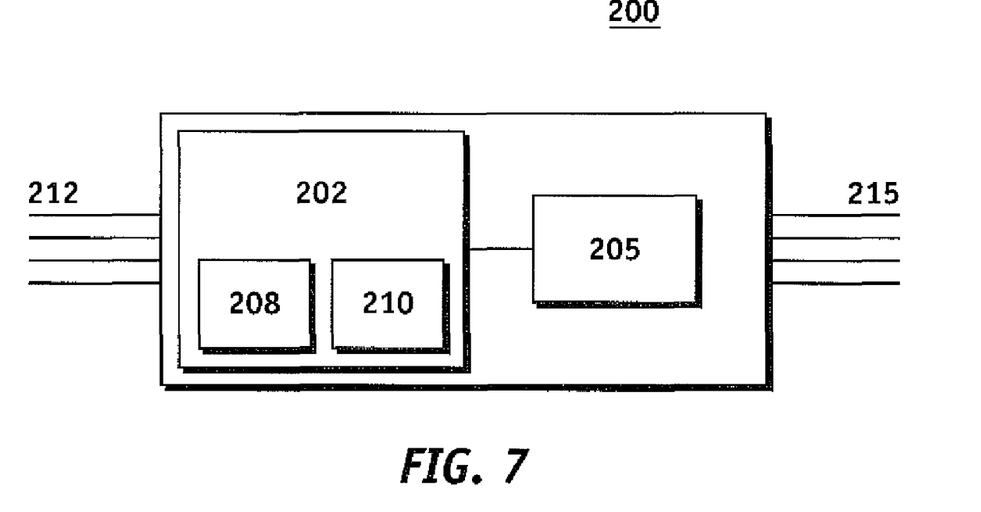
FIG. 7 is schematic diagram of a system for providing an ophthalmic element according an embodiment of the present invention.

Referring to FIG. 7, in certain embodiments of the present invention, a system 200 for producing an ophthalmic element comprises an electronic memory 202 coupled to a processor 205. Memory 202 includes a plurality of code modules 208 for execution by processor 205 and one or more data values 210 used during execution of code modules 208. The data values 210 may include data values for defining a model cornea and for defining a model ophthalmic element that are used in determining parameters suitable for providing an ophthalmic element according to one or more embodiments of the present invention. System 200 may further include an input 212, for example, to provide data values 210 and/or at least portions of code modules 208. System 200 may also include an output 215 that includes parameters suitable for use in fabricating or realizing a physical ophthalmic element. In certain embodiments, the processor 205 is used carry out all or portions of method 100 discussed above and shown in FIG. 6.

The processor 205 may be any electronic chip or circuit suitable for making calculating necessary to provide an ophthalmic element according to one or more embodiments of the present invention. Although not required, the processor 205 and electronic memory 202 will commonly be integrated into a single system such as a desktop or portable computer, or some other specialized electronic system.

Data values 210 of memory 202 for defining the model cornea may include, but is not limited to, one or more of:
  Data for an aspheric profile along a first meridian of the model cornea that is different from an aspheric profile along a second meridian of the model cornea.
  Data for one or more of fifth-order, seventh-order, and ninth-order aberrations.
  Data for an asphericity of a first zone of the model cornea that is different from an asphericity of a second zone of the model cornea surrounding the first zone.

In the last instance, the first zone may be or represent the area of an individual cornea or average cornea over which a corneal refractive procedure has been performed, while the second zone may be an area of the cornea that is unaffected by the corneal refractive procedure.

Data values 210 of memory 202 for defining the model ophthalmic element comprising an anterior surface and an opposing posterior surface, wherein the model ophthalmic element is characterized by a higher order toric shape imposed on one of the surfaces, the higher order toric shape including a primary meridian characterized by a first profile and a secondary meridian characterized by a second profile that is different from the first profile, the higher order toric shape being characterized by a profile along at least one meridian that changes according to radius from the optical axis raised to a power that is greater than two.

Code modules 208 may include, but not limited to:

One or more code modules for calculating a merit function representative of the optical performance of a system including the model cornea and the model ophthalmic element;

One or more code modules for selecting a value of a first coefficient of an equation characterizing the higher order toric shape of the model ophthalmic element;

One or more code modules for calculating a value of the merit function based on the value of the first coefficient and determining whether the value of the merit function is above a predetermined value.

One or more code modules for repeating selecting a value of the first coefficient and calculating a value of the merit function until the merit function is above the threshold value.

One or more code modules for providing parameters necessary to produce a physical ophthalmic element, the parameter values being based on a value of the first coefficient that causes the merit function to be above the threshold value.

Output 215 may include one or more of a monitor displaying values for the parameters, one or more sheets of paper containing values for the parameters, and an electronic signal containing values of the parameters that are readable by a receiving electronic device used in providing the ophthalmic element. For example, the receiving electronic device may be a computer or processor that is used to calculate a treatment plan for controlling a laser during a corneal refractive procedure. Alternatively, the receiving electronic device may be a computer or processor that is used to control, or provide input to, a machine used to produce an optic element or a mode used to produce an optical element.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. An ophthalmic lens, comprising:
    an optic body disposed about an optical axis having a primary meridian and an orthogonal secondary meridian, the optic body comprising an anterior surface and an opposing posterior surface, the optic body including an optic zone comprising a base shape configured to form an image from light incident on the surfaces;
    a base toric shape imposed on one of the surfaces, the base toric shape including a low power meridian having a low optical power and a high power meridian having a high optical power equal to the low optical power plus a cylinder optical power; and
    a higher order toric shape imposed on one of the surfaces, the higher order toric shape including a first profile disposed along the primary meridian and a second profile disposed along the secondary meridian that is different in shape from the first profile, the higher order toric shape being characterized by a profile along at least one meridian of the ophthalmic lens that changes with increasing radius from the optical axis raised to a power that is greater than two.

2. The ophthalmic lens of claim 1, wherein the profile of the higher order toric shape along at least one meridian of the optic body is characterized by a polynomial equation including a term that changes according to radius from the optical axis raised to a power that is greater than two.

3. The ophthalmic lens of claim 1, wherein at least one of the anterior surface and the posterior surface includes an axisymmetric aspheric shape characterized by a conoid of rotation defined by a profile defined by a base curvature and a conic constant.

4. The ophthalmic lens of claim 3, wherein one of or both the higher order toric shape are located on one surface of the optic body and the axisymmetric aspheric shape is located an opposite surface of the optic body.

5. The ophthalmic lens of claim 1, wherein the primary meridian is coplanar in a plane parallel to the optical axis with one of the low power meridian and the high power meridian.

6. The ophthalmic lens of claim 1, wherein the base toric shape and the higher order toric shape are disposed on a same surface of the optic body.

7. The ophthalmic lens of claim 1, wherein the base toric shape is characterized by the equation:

$$z = A_{20}x^2 + A_{11}xy + A_{02}y^2$$

where x and y are independent coordinate values along an x-axis and a y-axis, respectively, z is a surface coordinate value along a z-axis that is perpendicular to the x and y axes, and $A_{20}$, $A_{11}$, and $A_{02}$ are polynomial coefficients of the equation, at least two of the polynomial coefficients being non-zero.

8. The ophthalmic lens of claim 1, wherein a sag z of the anterior surface or the posterior surface is characterized by the equation:

$$z = \frac{cr^2}{1 + \sqrt{1-(1+k)c^2r^2}} + A_{20}x^2 + A_{02}y^2 + A_{40}x^4 + A_{04}y^4 + A_{22}x^2y^2 + A_{60}x^6 + A_{06}y^6 + A_{42}x^4y^2 + A_{24}x^2y^4$$

where x and y are independent coordinate values along an x-axis and a y-axis, respectively, z is a surface sag coordinate value along a z-axis perpendicular to the x and y axes, $r^2$ is equal to $x^2+y^2$, c is a base curvature, k is a conic constant, and $A_{20}$, $A_{02}$ are polynomial coefficients characterizing the base toric shape, and $A_{40}$, $A_{04}$, $A_{22}$, $A_{60}$, $A_{06}$, $A_{42}$, and $A_{24}$ are polynomial coefficients characterizing the higher order toric shape, wherein one or more of the following is true:

one or more of $A_{22}$, $A_{42}$, and $A_{24}$ is non-zero;

one or more of $A_{40}$ and $A_{04}$ is non-zero, wherein $A_{40}$ does not equal $A_{04}$;

one or more of $A_{60}$ and $A_{06}$ is non-zero, wherein $A_{60}$ does not equal $A_{06}$; and the equation includes at least one non-zero polynomial term that includes at least one of x raised to an odd power and y raised to an odd power.

9. The ophthalmic lens of claim 8, wherein the odd power is 1, 3, 5, or 7.

10. The ophthalmic lens of claim 1, wherein a sag z of the anterior surface or the posterior surface is characterized by the equation:

$$z = \frac{cr^2}{1 + \sqrt{1 - (1+k)c^2 r^2}} + A_{20}x^2 + A_{11}xy + A_{02}y^2 + A_{30}x^3 + A_{03}y^3 + A_{40}x^4 + A_{04}y^4 + A_{22}x^2 y^2 + A_{60}x^6 + A_{06}y^6 + A_{42}x^4 y^2 + A_{24}x^2 y^4$$

where x and y are independent coordinate values along an x-axis and a y-axis, respectively, z is a surface sag coordinate value along a z-axis perpendicular to the x and y axes, $r^2$ is equal to $x^2+y^2$, c is a base curvature, k is a conic constant, $A_{11}$ is a polynomial coefficient characterizing the base toric shape, and $A_{30}$ and $A_{03}$ are polynomial coefficients characterizing the higher order toric shape, wherein at least one of $A_{11}$, $A_{30}$ and $A_{03}$ are non-zero.

11. The ophthalmic lens of claim 8, wherein the values of one or more of k, $A_{20}$, $A_{02}$, $A_{40}$, $A_{04}$, $A_{22}$, $A_{60}$, $A_{06}$, $A_{42}$, and $A_{24}$ are determined based on a corneal shape, the corneal shape being selected from the group consisting of the shape of a cornea of a particular eye and an average corneal shape of a population of eyes.

12. The ophthalmic lens of claim 1, wherein the higher order toric shape is characterized by the equation:

$$z = A_{40}x^4 + A_{04}y^4 + A_{22}x^2 y^2 + A_{60}x^6 + A_{06}y^6 + A_{42}x^4 y^2 + A_{24}x^2 y^4$$

where x and y are independent coordinate values along an x-axis and a y-axis, respectively, z is a surface coordinate value along a z-axis that is perpendicular to the x and y axes, and $A_{40}$, $A_{04}$, $A_{22}$, $A_{60}$, $A_{06}$, $A_{42}$, and $A_{24}$ are polynomial coefficients of the equation.

13. The ophthalmic lens of claim 1, wherein a sag z of the anterior surface or the posterior surface is characterized by the equation:

$$z = \frac{cr^2}{1 + \sqrt{1 - (1+k)c^2 r^2}} + A_{40}x^4 + A_{04}y^4 + A_{22}x^2 y^2 + A_{60}x^6 + A_{06}y^6 + A_{42}x^4 y^2 + A_{24}x^2 y^4$$

where x and y are independent coordinate values along an x-axis and a y-axis, respectively, z is a surface sag coordinate value along a z-axis perpendicular to the x and y axes, $r^2$ is equal to $x^2 + y^2$, c is a base curvature, k is a conic constant, and $A_{20}$, $A_{11}$, $A_{02}$ are polynomial coefficients characterizing the base toric shape, and $A_{40}$, $A_{04}$, $A_{22}$, $A_{60}$, $A_{06}$, $A_{42}$, and $A_{24}$ are polynomial coefficients characterizing the higher order toric shape, wherein one or more of the following is true:

one or more of $A_{22}$, $A_{42}$, and $A_{24}$ is non-zero;

one or more of $A_{40}$ and $A_{04}$ is non-zero, wherein $A_{40}$ does not equal $A_{04}$;

one or more of $A_{60}$ and $A_{06}$ is non-zero, wherein $A_{60}$ does not equal $A_{06}$; and the equation includes at least one non-zero polynomial term that includes at least one of x raised to an odd power and y raised to an odd power.

14. The ophthalmic lens of claim 1, wherein a sag z of the anterior surface or the posterior surface is characterized by the equation:

$$z = \frac{c_1 x^2 + c_2 y^2}{1 + \sqrt{1 - (1+k_1)c_1^2 x^2 + (1+k_2)c_2^2 x^2}} + A_{40}x^4 + A_{04}y^4 + A_{22}x^2 y^2 + A_{60}x^6 + A_{06}y^6 + A_{42}x^4 y^2 + A_{24}x^2 y^4$$

where x and y are independent coordinate values along an x-axis and a y-axis, respectively, z is a surface sag coordinate value along a z-axis perpendicular to the x and y axes, $r^2$ is equal to $x^2 + y^2$, where $c_1$ is the base curvature along a first meridian of the optic body, $k_1$ is the conic constant along the first meridian, $c_2$ is the base curvature along a second meridian of the optic body, $k_2$ is the conic constant along the second meridian, and $A_{40}$, $A_{04}$, $A_{22}$, $A_{60}$, $A_{06}$, $A_{42}$, and $A_{24}$ are polynomial coefficients characterizing the higher order toric shape, wherein one or more of the following is true:

one or more of $A_{22}$, $A_{42}$, and $A_{24}$ is non-zero;

one or more of $A_{40}$ and $A_{04}$ is non-zero, wherein $A_{40}$ does not equal $A_{04}$;

one or more of $A_{60}$ and $A_{06}$ is non-zero, wherein $A_{60}$ does not equal $A_{06}$; and the equation includes at least one non-zero polynomial term that includes at least one of x raised to an odd power and y raised to an odd power.

15. The ophthalmic lens of claim 1, wherein the ophthalmic lens is an intraocular lens including one or more haptics extending from the optic body.

16. The ophthalmic lens of claim 1, wherein the ophthalmic lens is selected from the group consisting of an intraocular lens, a contact lens and, a corneal implant.

17. An ophthalmic lens, comprising:

an optic body disposed about an optical axis having a primary meridian and an orthogonal secondary meridian, the optic body comprising an anterior surface and an opposing posterior surface, the optic body including an optic zone comprising a base shape configured to form an image from light incident on the surfaces;

a base toric shape imposed on one of the surfaces, the base toric shape including a low power meridian having a low optical power and a high power meridian having a high optical power equal to the low optical power plus a cylinder optical power;

wherein at least one of the anterior surface and the posterior surface includes an axisymmetric aspheric shape characterized by a conoid of rotation defined by a profile defined by a base curvature and a conic constant.

18. The ophthalmic lens of claim 17, wherein the base toric shape is characterized by the equation:

$$z = A_{20}x^2 + A_{11}xy + A_{02}y^2$$

where x and y are independent coordinate values along an x-axis and a y-axis, respectively, z is a surface coordinate value along a z-axis that is perpendicular to the x and y axes, and $A_{20}$, $A_{11}$, and $A_{02}$ are polynomial coefficients of the equation, at least two of the polynomial coefficients being non-zero.

19. The ophthalmic lens of claim 17, wherein the ophthalmic lens is an intraocular lens including one or more haptics extending from the optic body.

20. The ophthalmic lens of claim 17, wherein the ophthalmic lens is selected from the group consisting of an intraocular lens, a contact lens and, a corneal implant.

* * * * *

UNITED STATES PATENT AND TRADEMARK OFFICE
CERTIFICATE OF CORRECTION

PATENT NO. : 8,256,896 B2  
APPLICATION NO. : 12/713046  
DATED : September 4, 2012  
INVENTOR(S) : Huawei Zhao Page 1 of 1

It is certified that error appears in the above-identified patent and that said Letters Patent is hereby corrected as shown below:

On the title page, Item (73) Assignee should read: Abbott Medical Optics Inc., Santa Ana, CA (US)

Signed and Sealed this  
Thirty-first Day of December, 2013

Margaret A. Focarino  
*Commissioner for Patents of the United States Patent and Trademark Office*